United States Patent [19]

Karuhn

[11] 4,036,212

[45] July 19, 1977

[54] METHOD OF PREDETERMINING TIME OF OVULATION IN WOMEN AND IN ANIMALS TO CONTROL CONCEPTION

[76] Inventor: Richard F. Karuhn, 1705 W. 61st St., Downers Grove, Ill. 60515

[21] Appl. No.: 731,348

[22] Filed: Oct. 12, 1976

Related U.S. Application Data

[63] Continuation-in-part of Ser. No. 643,036, Dec. 22, 1975, abandoned.

[51] Int. Cl.$^2$ .............................................. A61B 10/00
[52] U.S. Cl. ................... 128/2 R; 23/230 B; 128/2 W
[58] Field of Search ............. 128/2 R, 2 W; 23/230 B

[56] References Cited

U.S. PATENT DOCUMENTS

| | | | |
|---|---|---|---|
| 3,037,496 | 6/1962 | Melges | 128/2 W |
| 3,406,015 | 10/1968 | Foster | 128/2 W X |
| 3,940,250 | 2/1976 | Plakos et al. | 23/230 B |

Primary Examiner—Kyle L. Howell
Attorney, Agent, or Firm—Darbo, Robertson & Vandenburgh

[57] ABSTRACT

The achievement of conception and the sex of the resulting human baby depends upon, or is influenced by, the time of impregnation with respect to the time of ovulation. Predetermination of prospective ovulation time enhances success since impregnation should precede ovulation because sperm remains viable longer than the egg. On the basis of the discovery that vaginal fluid contains ATP not only in women but also in a class of mammals, e.g., cows, and that the concentration varies in repeated patterns in successive ovulation cycles, the time of ovulation is predicted by measurement of ATP concentration. This is done quantitatively and reliably by measuring the intensity of light resulting from the reaction of ATP with luciferase/luciferin. A suitable buffer effects protraction of light for accurate reading with a simple meter.

10 Claims, 1 Drawing Figure

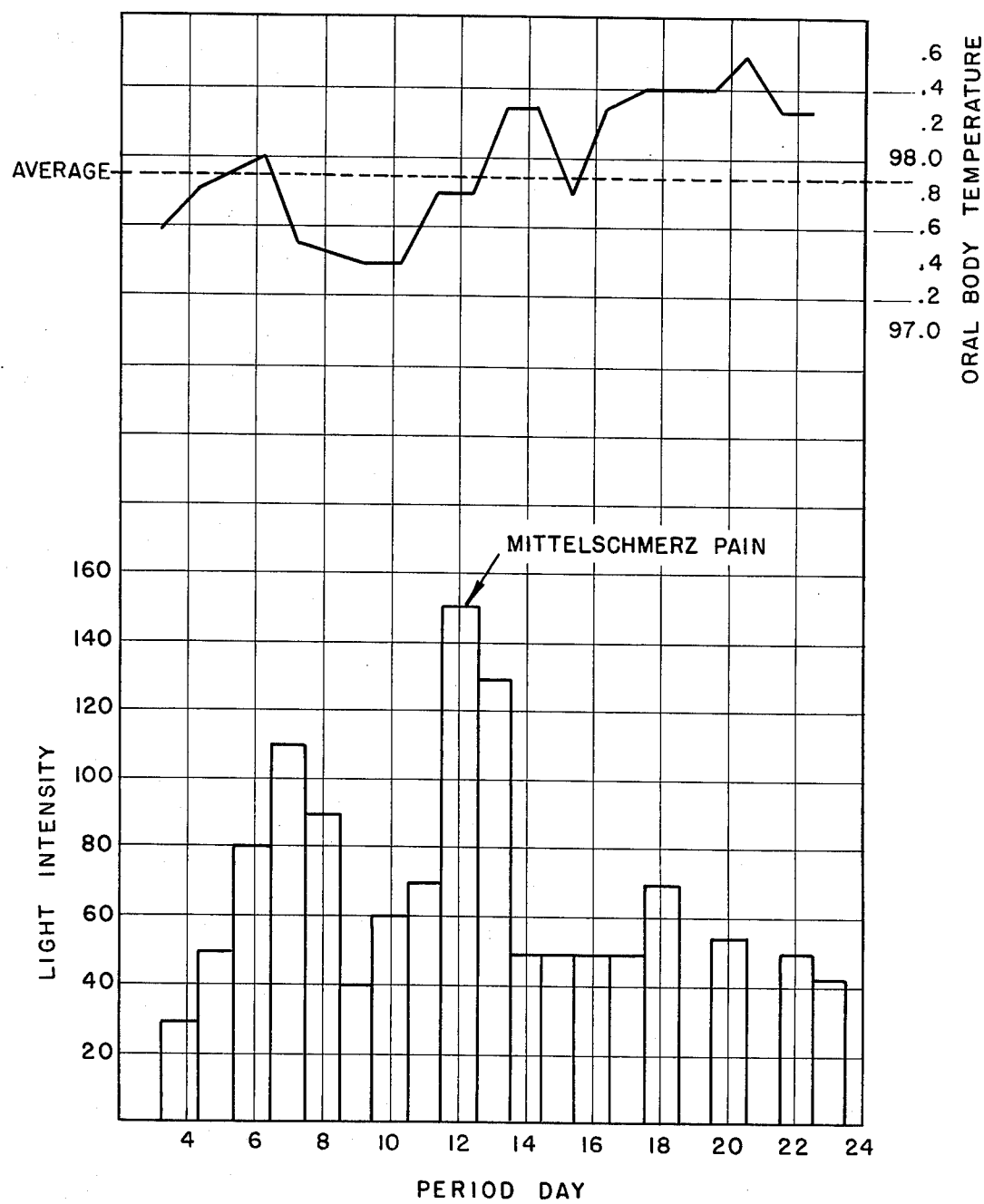

METHOD OF PREDETERMINING TIME OF OVULATION IN WOMEN AND IN ANIMALS TO CONTROL CONCEPTION

RELATED APPLICATION

This application is a continuation-in-part of application Ser. No. 643,036, filed Dec. 22, 1975, now abandoned.

PREFACE TO THIS DISCLOSURE

For maximum clarity, the application of the invention will first be described in detail with reference to women. The parallel application to animals will follow.

BACKGROUND AND SUMMARY OF THE INVENTION

To some degree, man has probably always desired to control conception, avoiding fertilization of the ovum without refraining from sexual intercourse if a baby is not wanted and achieving fertilization if a baby is wanted. Increasing concern in recent years about the prospect of overpopulation of the entire world has intensified the interest in family planning and conception control. On the other hand, many women desiring children are unable, without taking special measures, to achieve pregnancy. Thus, the control of conception involves both the achievement and the avoidance of conception, not on the basis of chance, but in accordance with the desires of the individuals involved.

Another aspect of conception control relates to the production of a boy or a girl baby. To varying degrees and in different ways, different cultures have followed practices thought to influence the sex of the baby to be conceived. Only in recent years, however, has this subject been given scientific treatment. It has been demonstrated that the probabilities of producing a baby of a desired sex may be enhanced by following certain procedures and practices.

An important consideration in both aspects of conception control is the timing of impregnation relative to the time of ovulation. Since the sperm is viable in the woman's reproductive organs for, perhaps, 4 or 5 days, and the ovum is viable for about 7 hours, it follows that intercourse more than 5 days before, or more than 7 hours after, ovulation cannot result in conception. This is the basic concept of the so-called rhythm method of birth control (which is only about 75 per cent effective due largely to the inability to predict the exact time of ovulation). The indispensability, then, of the coexistence of both the sperm and the ovum in the women's reproductive tract indicates the necessity of predetermining the time of ovulation which is the uncontrollable but controlling factor since the time of impregnation, whether by natural coitus or artificial impregnation, can, presumably, be controlled accordingly by the participants.

The sex of the conceived baby is the result of many factors and coincidences, only some of which are known. It has been observed that, in general, the semen contains both sperm carrying the male-producing Y chromosomes (androsperms) and sperm carrying the female-producing X chromosomes (gynosperms), the former usually initially predominating in number and mobile activity. While there is not yet full agreement among researchers of the effect of time of impregnation during the fertile period, and investigation is continuing, there appears to be full agreement that the time of natural impregnation or artificial insemination with respect to the time of ovulation affects the probabilities of having a boy baby or a girl baby, probably due to the effect of vaginal environmental factors on sperm viability. Thus, again, the predetermination of the time of ovulation is indispensable to the achievement of the desired result.

The ovulation cycle is controlled by four hormones, the most important of which is estrogen. This is a powerful hormone with several important functions in a woman's body. Flowing in the bloodstream, it performs a messenger service, signaling and triggering a complicated program of activity. Estrogen also stimulates the lining of the uterus, it acts on the vaginal mucosa and it stimulates secretion of an abundant translucent glair from the cervical glands necessary for the transport of sperm into the uterus.

The second hormone, follicle stimulating hormone (FSH), is dispatched from the pituitary. Liberation of this hormone appears to be controlled by the estrogen level from the previous cycle. FSH causes a single follicle in the ovary to grow. As the follicle matures it liberates estrogen in quantities which increase daily. This process is self-stimulating and causes a rapid build-up of estrogen in the blood during the period preceding ovulation.

The third hormone, lutenizing hormone (LH), is liberated from the pituitary gland when the estrogen content of the blood has reached a relatively high level. The LH surge induced by a rapid drop in estrogen level, contributes to a further swelling of the pre-ovulatory follicle.

The events leading to ovulation are completed when follicular rupture occurs with the liberation of an ovum. Thereafter, the estrogen content of the blood plasma continues to drop rapidly. The ruptured follicle turns into a body called the corpus luteum.

The corpus luteum now secretes estrogen as the follicle did, but it also secretes progesterone, the fourth hormone in the cycle. Progesterone stimulates more elaborate changes in the uterus to prepare it to receive a fertilized egg. The production of estrogen by the corpus luteum results in a second plateau of estrogen in the blood. Maturity of the corpus luteum is reached followed by its gradual regression with corresponding reduction in steroid secretion.

While the particular pattern of activity differs with different individuals, it repeats its characteristic form, cycle after cycle, in the body of a particular woman, absent disturbing influences. Charts can be, and have been, made showing consecutive daily levels of estrogen in the blood plasma and relating the resulting pattern with the time of ovulation. These charts show that the estrogen content of the blood peaks at least a day or two before ovulation, in some cases as much as 72 hours prior to ovulation. The estrogen level increases day by day until the peak level is reached, then rapidly decreases in advance of ovulation. Once the characteristic chart of a particular individual has been established by daily plasma tests over, perhaps, 3 or 4 months, it is possible thereafter to predict the time of ovulation well in advance of the occurrence. However, the determination of estrogen content in blood plasma requires laboratory procedure beyond the ability and facilities of a lay woman. For this reason it is not practical to employ estrogen level charts to predetermine ovulation time.

It is known that a woman's body temperature also varies in repeated patterns as the events of the ovulation cycle occur. Normally, the pre-ovulatory level of temperature is below average throughout that particular phase of the menstrual cycle and will rise or fall a small fraction of a degree over succeeding days. A sudden drop of a few tenths of a degree (F.) or more signals that ovulation is imminent and a succeeding sharp rise of a degree or so to a new plateau well above the average temperature of the full cycle indicates that ovulation has taken place. As a guide to the timing of impregnation, the temperature charts are not satisfactory because indications are both too late and not sufficiently certain.

The object and achievement of the present invention is to provide a method of predetermining the time of ovulation by means and procedures which are so simple that the ordinary woman can make her own determination.

The method of this invention is based upon the discoveries that the vaginal fluid contains adenosine triphosphate (ATP) and that the concentration of ATP in the vaginal fluid varies from day to day throughout the ovulation cycle much as, in women, the estrogen level in blood plasma varies, especially during the critical ovum-forming period immediately preceding ovulation. The inventive concept involves the interval determination, as day by day, of ATP level in the vaginal fluid from which the time of ovulation can be predetermined as above described with reference to estrogen level but by simpler and less costly procedures. ATP levels are determined by measuring the intensity of light resulting from the reaction of the ATP content of successive, e.g. daily, samples of vaginal fluid with luciferase/luciferin in the presence of magnesium and manganese ions. The ease and accuracy of measurement of the light intensity by means of a simple meter is enhanced by buffering the solution to stabilize and prolong the life of the light emission.

For many reasons, artificial insemination is preferred to natural mating in both beef and dairy cattle but the cost is substantial and dependence upon observation of vaginal mucous discharge to signal estrous is unsatisfactory. The rapid development of the impregnation of cows (including heifers) by artificial insemination magnifies the importance of determining the time of ovulation by improved means to maximize the probability of effecting pregnancy.

At the present time, there are about 20,000,000 cows in the United States. In the year 1975, approximately 50 percent of the cows were artificially inseminated. The pregnancy rate resulting from natural mating at a single estrous in beef cattle averaged 70 percent while this average was 60 percent for artificial insemination. A principal reason for these low pregnancy rates is the failure to provide spermatozoa in the cows' reproductive tract at the time of ovulation; that is, impregnation at the wrong time.

In the bovine female, the ovulation cycle is controlled by hormonal interaction differing from that in women but similar for the purposes of the present invention in that the concentration of ATP in the vaginal fluid varies with the ovulation cycle so that the procedures herein described for determining the time of ovulation in women are directly applicable to determine the time of ovulation in cows. While the LH surge appears to respond to the level of estrogen in the blood in women, a similar release of LH appears to result from a precipitous decrease in the presence of progesterone in the blood plasma and milk in the case of cows. The rapid reduction in progesterone content signals LH release and estrous followed by ovulation. Thus, in the bovine female ovulation takes place while the estrogen titer is high whereas in women the estrogen content drops before the LH surge and continues to drop precipitously just before ovulation takes place. The presence of ATP similarly varies measurably at the critical time prior to ovulation.

The general object of the invention, then, is to provide a practical means for predetermining with reasonable accuracy and a sufficient time in advance of the event the time of ovulation in women and in mammals having ovulation cycles, so that known procedures and principles, which depend for their effectiveness on such predetermination of the time of ovulation, may be employed to control the probabilities of conception and/or the sex of the conceived baby, in the case of women, and to insure pregnancy in animals. The technique of the invention may also serve as a diagnostic aid to the gynecologist in establishing management procedures to meet the needs of abnormal reproductive conditions in some women.

More specifically, an object of the invention is to provide a method for predetermining the time of ovulation in women by interval charting of the intensity levels of light chemically produced from the ATP content of samples of vaginal fluid taken at intervals over at least the ovum-forming period. The predetermination is made by comparison with previously prepared charts for the same individual showing the time of ovulation in relation to the chart form, this time having been determined by any of several indications, such as the Mittelschmerz pain, temperature shift method, etc.

Another object is to provide a practical method for predetermining the time of ovulation in cows to thus determine the best time for insemination for effecting pregnancy.

Further objects include the provision of techniques and means for simplifying and increasing the accuracy of light intensity determinations and thereby the accuracy of ATP level determinations.

DESCRIPTION OF THE DRAWING

The accompanying drawing is a daily interval chart showing light intensity readings (and thus vaginal fluid ATP content) over periods several days before and several days after ovulation as taken by and for a particular woman. Body temperature variations over the same period of time are shown for comparison purposes.

DESCRIPTION OF SPECIFIC METHOD

As has already been indicated, the method of this invention for predetermining the time of ovulation in women requires the determination of certain changes in the body which have a demonstrable relationship to the event of ovulation. More specifically, the changing level of the ATP concentration in the vaginal fluid is monitored to provide a pattern of change which has been shown to be meaningful from the standpoint of the prediction of time of ovulation. The usually marked reduction in ATP content following a daily build-up to a peak level indicates maturation of the ovum and ovulation. Because the timing and magnitude of the events of the cycle differ greatly for different women, it is not possible to establish a standard reference chart showing, for example, daily ATP levels with an indication of the time of ovulation on the time coordinate. It is necessary that each individual establish such a chart for herself which can then be used for reference purposes in the interpretation of the monitoring data when it is desired to implement a program to enjoy the benefits of the method of this invention.

Recommended procedure includes the determination and charting of the daily levels of ATP for at least several days before and several days after ovulation for a period encompassing three or four cycles. The purpose is to establish the chart profile of the particular individual and to locate the time of ovulation on the reference chart. The manner of determining ATP levels will be described in detail hereinafter. For those women who experience and recognize the Mittelschmerz pain, this is the best indicator of the fact of ovulation. Other methods of indicating the time include testing by means presently known and available to determine the presence of glucose which appears in substantial quantity in the cervical mucous at about the time of ovulation, or by the body temperature observation method.

Having prepared a standard reference chart, the woman is in a position to predetermine the time of her next ovulation in accordance with the method of this invention. The recommended procedure is for her to make daily determinations of ATP level, marking the readings on a chart so that she can observe the direction and magnitude of day-to-day changes. A typical chart is that shown in the drawing. Although this chart shows readings from day 4 through day 23 (day 1 of the ovulation cycle being the first day of her menstrual period), it is not necessary to continue the daily tests after, say, day 14 since the clearly perceptible drop in ATP level is noted on day 13 and confirmed on day 14. The readings recorded are those taken directly from a light meter which measures the intensity of the light which results from the photochemcial reaction of the ATP contained in a vaginal fluid specimen.

The supplies and equipment needed for the taking and preparation of the samples and to take the light intensity readings include swabs, a glass vial, buffer solution, the luciferase/luciferin photochemical reagent, and a light meter. A swab is used to obtain a sample of vaginal fluid. Since the light intensity reading reflects the concentration of ATP in the test sample, it is necessary to provide a certain amount of fluid for each test. It is also desirable to collect only clear liquid without cloudy mucous which tends to interfere with the eventual light reading. It has been found that by using ready-made cotton swabs, such as those sold under the trademark "Q-tip", and inserting the swab into a finely apertured cylindrical filter element to exclude cloudy mucuous material and leaving this sampler in the vagina for a period of about one-half of a minute to saturate the swab, the quantity of the fluid sample withdrawn with the swab is such that dependable results are obtainable. Although the viscosity and possibly other dimensional aspects of the vaginal fluid varies at different times in the ovulation cycle, the important comparison is between the reading for a particular day with preceding days of the cycle. When a comparison of the day's test results reveal the telltale build-up of ATP, the fertile period has been reached and ovulation will follow shortly and occur as the concentration of ATP decreases substantially.

The following is a specific example of a practical and useful program for implementing the method of the invention. On the first day after menstrual bleeding stops, the woman takes a sample of vaginal fluid using a suitable standard swab encased in its filter. The loaded swab is inserted into a vial containing 1 ml. of buffer solution and mixed well into the solution using the swab to stir. The swab is then withdrawn and discarded and luciferase/luciferin reagent is added to the solution from a capable containing 5 mg. of the material. The vial is then placed into the light meter and the intensity of the light resulting from the reaction is read on the meter scale and entered on a chart.

This procedure is followed at appromimately the same time day after day until the light intensity readings show a substantial build-up of ATP in the vaginal fluid. Further daily readings may be taken and charted, if desired, to confirm the peaking of the ATP concentration and the post peak drop, but such additional readings are usually not necessary since the telltale information has already been developed.

By comparing the working chart thus prepared with the previously established standard chart showing the relationship of the time of ovulation with the preovulation chart profile, the woman, having observed the telltale build-up in the light intensity of her daily samples, can predict the time when she will ovulate and, if desired, can confirm that ovulation has occurred.

The photochemical reaction of ATP with the luciferase/liciferin reagent is known and has been used for assay purposes. The light-producing reaction is represented by Katherine F. Daly in an article in the December, 1974, issue of American Laboratory Magazine, page 38, as follows:

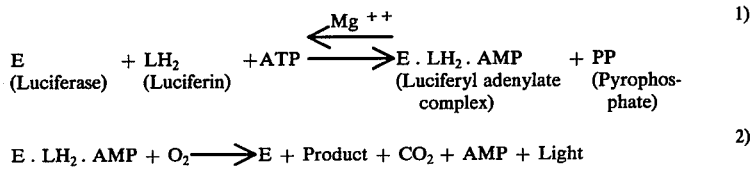

$$E + LH_2 + ATP \underset{}{\overset{Mg^{++}}{\rightleftarrows}} E \cdot LH_2 \cdot AMP + PP \qquad 1)$$
$$\text{(Luciferase)} \quad \text{(Luciferin)} \qquad \qquad \text{(Luciferyl adenylate complex)} \quad \text{(Pyrophosphate)}$$

$$E \cdot LH_2 \cdot AMP + O_2 \longrightarrow E + \text{Product} + CO_2 + AMP + \text{Light} \qquad 2)$$

Commercial American Firefly (Photinus Pyrolis) Luciferin is available. The material is a mixture of purified enzyme luciferase and synthetic substrate luciferin. Increasing the luciferin concentration in the test samples increases, in general, the intensity of light from a given quantity of ATP. It is necessary, therefore, that this concentration should remain constant throughout any test series. It has been found that the desirable range of concentration is from 5 to 10 mg. of the luciferin powder to 1 ml. of buffer solution.

The buffer system developed for use with the testing procedures of the invention was designed to (1) provide a light signal sufficiently prolonged, yet constant, to permit easy and accurate readings on the light meter and (2) maintain a stable pH while promoting the development of a high light level. The preferred buffer is prepared as follows: A 1.5 molar aqueous solution of glycine is adjusted to a pH of 8.0 using LiOH solution or purified choline base, and $MgSO_4$ and $MnSO_4$ are added to the solution in the amount of $1 \times 10^{-3}$ molar for each material.

Commercial choline base is supplied in a methanol solvent which appears to inhibit the full development of light in the photochemical reaction. To purify this commercial material, the methanol is removed by stripping under vacuum. The thick black residue is thinned down with water and exposed to a LiOH activated cation exchanger resin such as that available under the trade designation Rexin RG1 (OH), Fisher Catalog No. R-205. The solution resulting from the exchange reaction is water white and ready to be used for adjusting the pH of the glycine solution as above described.

Other known buffers may be used to maintain the optimum pH level of the test solution to provide the most readable light signal.

The bovine ovulaton cycle is 21 days or very nearly so. Over this period, the progesterone content in the milk and in the blood plasma increases approximately fivefold to a generally midpoint plateau, then decreases quite precipitiously to a minimum level at estrous and ovulation. Also, in most cows, the LH level peaks approximately at estrous. Most important for the purposes of the present invention, the level of ATP in the vaginal fluid was found to diminish rapidly with the approach to estrous. Test readings of light intensity using sampling techniques and procedures above described for from three to five days prior to the estimated time of estrous indicates the imminence of estrous. The subject cow is then observed for the telltale vaginal discharge. The cow is bred by articial insemination approximately 12 hours after the onset of estrous.

ACHIEVEMENT

It will be understood from the foregoing that the discoveries leading to the highly useful techniques herein disclosed provide means whereby human individuals may more dependably program their sex activities to carry out their desires in this area of male/female relationships. The probabilities of conception as a result of coitus may be enhanced or reduced as desired by the participants by applying information obtainable by use of the methods of the invention. In another aspect of conception control, the sex of the baby resulting from either natural impregnation or artificial insemination may be influenced to some degree with intelligent use of this information.

The fundamental achievement of the invention resides in the additional means rendered available to follow, and to a substantial extent predict, the pattern of events in the reproductive cycle of a woman. It is also possible to determine the point of progress at any particular time of the cycle. Thus, the discoveries and methods of the invention provide aids to the gynecologist which, along with information already available, enable the medical experts to provide useful advice and procedures to enable individuals to achieve their desires in the area of reproduction. They constitute additional diagnostic tools and provide an additional dimension for the establishment of prophylactic or remedial programs of action.

As applied to cows, and to other mammals having corresponding estrous cycles, the methods of the invention provide greatly increased efficiency in the management of breeding by indicating by practical testing procedures the approach of estrous.

I claim:

1. The method of monitoring the progress of the ovulation cycle of a female mammal of the kind having an ovulation cycle which comprises periodically determining the concentration of ATP in the mammal's vaginal fluid over the period of desired investigation by measuring the intensity of light resulting from the reaction of the ATP content of periodically taken samples of the fluid with luciferase/luciferin in the presence of magnesium and manganese ions.

2. The method of claim 1 wherein the reaction solution is buffered to stabilize its pH and protract the light signal resulting from the reaction.

3. The method of claim 2 wherein the buffer comprises a 1.5 molar aqueous solution of glycine adjusted to a pH of 8.0 with purified choline base with $MgSO_4$ and $MnSO_4$ added in the amount of $1 \times 10^{-3}$ molar for each material.

4. The method of claim 2 wherein the buffer comprises a 1.5 molar aqueous solution of glycine adjusted to a pH of 8.0 with LiOH with $MgSO_4$ and $MnSO_4$ added in the amount of $1 \times 10^{-3}$ molar for each material.

5. The method of claim 2 wherein each determination is carried out as follows: a standard sample of vaginal fluid is mixed with a standard quantity of buffer solution in a vial, a standard quantity of luciferase/luciferin reagent is added to the solution, and the intensity of the light emitted from the solution is measured.

6. The method of claim 5 wherein the standard samples are taken by inserting a standard swab encased within a filter membrane into the vagina and permitting the swab to remain therein for a period of time sufficient to substantially fully load the swab with vaginal fluid.

7. The method of predetermining the time of ovulation of a woman which comprises periodically determining the concentration of ATP in the woman's vaginal fluid over at least her ovum development period by measuring the intensity of light resulting from the reaction of the ATP content of successive samples of the fluid with luciferase/luciferin in the presence of magnesium and manganese ions to indicate the trends of change in concentration of the ATP in the fluid.

8. The method of claim 7 and including the charting of the light intensity measurements for at least one full ovum development period to establish the general cycle profile for the individual for reference purposes in interpreting the significance of light intensity trends as measured during a subsequent ovum development period.

9. The method of predetermining the time of ovulation of a cow which comprises periodically determining the concentration of ATP in the cow's vaginal fluid during the period immediately preceding the cow's anticipated normal incidence of estrous by measuring the intensity of light resulting from the reaction of the ATP content of successive samples of the fluid with luciferase/luciferin in the presence of magnesium and manganese ions to indicate the trend of change in concentration of the ATP in the fluid and therefrom the imminence of estrous and thereafter placing the cow under surveillance and determining the onset of estrous and ensuing ovulation from externally visible sign.

10. The method of managing the breeding of a cow by artificial insemination which comprises the predetermination of the time of ovulation of the cow by the method of claim 9 and artificially inseminating the cow approximately 12 hours after the observed onset of estrous.

* * * * *

UNITED STATES PATENT AND TRADEMARK OFFICE
CERTIFICATE OF CORRECTION

PATENT NO. : 4,036,212
DATED : July 19, 1977
INVENTOR(S) : Richard F. Karuhn

It is certified that error appears in the above-identified patent and that said Letters Patent are hereby corrected as shown below:

| | |
|---|---|
| Col. 3, ls. 15 and 16 | "determination" should be --determinations-- |
| Col. 3, l. 51 | Sentence should not be broken into new paragraph |
| Col. 5, l. 36 | "photochemcial" should be --photochemical-- |
| Col. 5, l. 59 | "mucuous" should be --mucous-- |
| Col. 6, l. 14 | "capable" should be --capsule-- |
| Col. 6, l. 18 | "appromimately" should be --approximately-- |
| Col. 6, l. 34 | "liciferin" should be --luciferin-- |
| Col. 7, l. 17 | "ovulaton" should be --ovulation-- |
| Col. 7, l. 21 | "precipitiously" should be --precipitously-- |

Signed and Sealed this

Twenty-fifth Day of October 1977

[SEAL]

Attest:

RUTH C. MASON
Attesting Officer

LUTRELLE F. PARKER
Acting Commissioner of Patents and Trademarks